US006225803B1

(12) United States Patent
Chen

(10) Patent No.: US 6,225,803 B1
(45) Date of Patent: May 1, 2001

(54) NMR LOG PROCESSING USING WAVELET FILTER AND ITERATIVE INVERSION

(75) Inventor: Songhua Chen, Katy, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 09/182,624

(22) Filed: Oct. 29, 1998

(51) Int. Cl.[7] .......... G01V 3/00

(52) U.S. Cl. .......... 324/303; 324/300; 324/322

(58) Field of Search .......... 324/303, 300, 324/322; 348/397

(56) References Cited

U.S. PATENT DOCUMENTS

| | | | | |
|---|---|---|---|---|
| 4,933,638 | * | 6/1990 | Kleinberg et al. | 324/303 |
| 5,600,373 | * | 2/1997 | Chui et al. | 348/397 |
| 5,814,988 | * | 9/1998 | Itskovich et al. | 324/303 |

OTHER PUBLICATIONS

Paul Wallich, Wavelet Theory, Scientific American, Vol 1, pp 34–35, 1991.*

Chui et al, Wavelets on a Bounded Interval, vol 9 pp 53–75, 1992.*

* cited by examiner

*Primary Examiner*—Jay Patidar
*Assistant Examiner*—Brij B. Shrivastan
(74) *Attorney, Agent, or Firm*—Darryl M. Springs; Richard A. Fagin

(57) ABSTRACT

A method of nuclear magnetic resonance (NMR) well log processing. A wavelet decomposition of an NMR echo train is preformed. The resulting small scale coefficients, which may be discretely or continuously indexed by scale, in alternative embodiments, are windowed, and a first reconstruction generated therefrom by inverse wavelet transformation. The reconstructed signal is inverted and fit to a multiexponential model. Further refinements may be generated by iteratively decomposing the fitted signal at a preselected maximum scale, increasing at each iteration, generating a new coefficient by replacing the corresponding portion of the previous coefficient with the coefficient at the current scale, reconstructing the signal with the new coefficient, and fitting the signal so reconstructed to the relaxation time distribution.

40 Claims, 5 Drawing Sheets

NMR LOG PROCESSING USING WAVELET FILTER AND ITERATIVE INVERSION

BACKGROUND OF THE INVENTION

1. Field of the Invention

The invention relates generally to the field of well logging apparatus and methods, and in particular, to processing of nuclear magnetic resonance (NMR) signals to estimate physical properties of an oil or gas reservoir.

2. Description of the Related Art

Estimating physical parameters such as effective and total porosity, pore-size distribution, and the determining hydrocarbon types, are principal purposes for NMR log interpretation. The underlying rationale that NMR logging may provide such information is based on evidence that NMR relaxation times in porous media depend on texture (e.g., pore and grain-size distributions, in single wetting fluid phase saturated systems) and additionally on fluid types (oil/water/gas) in multiphase fluid-saturated porous media. Observed NMR log data (e.g., Carr, Purcell, Meiboom and Gill [CPMG] echo trains) represent the contributions from multiple fluid phases as well as fluids in different sized pores and thus, typically, exhibit a multiexponential behavior, with transverse relaxation times, $T_2$ components spanning from approximately one millisecond (ms) to over one second. The practical challenge for NMR log interpretation is to discriminate between contributions due to texture and fluid saturations and to quantify fluid saturations. Moreover, the NMR log signal typically is weak, and the instrumentation systems and the logging environment contribute significant noise that may be comparable to the signal. The resulting poor signal-to-noise ratio (S/N) gives rise to significant uncertainty in the estimated petrophysical parameters.

Prior art methods of NMR log interpretation generally use an inversion technique to estimate a relaxation distribution, i.e., a $T_2$ spectrum, from the acquired CPMG echo train data fit to a multiexponential decay relaxation distribution model. Different fluid phases may have different relaxation times, depending on the fluid molecular interaction, the rock surface properties, the reservoir environment, the fluid wetting characteristics of the formation and other physical properties known in the art. Distinctive features on the $T_2$ spectra, often reveal fluid saturations and pore structures—information on which petrophysical interpretation is based. For example, in the case of a water-wet reservoir with multiphase saturation, the non-wetting, and light, oil signal distributes into long relaxation bins. Water, on the other hand, in a water-wet reservoir, interacts strongly with pore surfaces, and thus has a short relaxation time. On a $T_2$ spectrum, water is identified from the short $T_2$ region, that is, initial bins. Gas, which is also non-wetting but diffuses faster than oil and water, may be identified in the intermediate region on a $T_2$ spectrum, since faster diffusion of gas reduces the apparent $T_2$ relaxation. From the estimated $T_2$ spectrum, partial porosities associated with different parts of the $T_2$ spectrum are identified for estimating the fluid saturations in a multiphase zone. In a single wetting fluid phase zone, for example, a water zone, with relative homogenous rock mineralogy, a $T_2$ spectrum approximately represents the porosity distribution in terms of pore sizes. Therefore, reliable interpretation depends heavily on accurate $T_2$ spectrum estimation.

It is well known that inverting echo train data to the $T_2$ domain distribution is an ill-conditioned problem, particularly when noise is present. Although regularization methods may help to stabilize the solutions, they also smooth the $T_2$ distribution estimate considerably, causing most of the distinguishing features of the $T_2$ distribution to be lost. The possible distortion of the resulting $T_2$ distribution estimate makes it difficult to separate the saturating fluid types. Furthermore, when a distribution involves short and long $T_2$ components, the standard procedure of using the method of minimization of least squares residuals in the inversion process often fails to weight all of the $T_2$ components equally. The short $T_2$ components are effectively represented by fewer echoes than the long $T_2$ components. When a $T_2$ distribution is dominated by a very short $T_2$ component and a second, long $T_2$ component, the technique can fail to fit the short component faithfully.

FIG. 1A shows data from a synthesized noisy echo train fitted to a multiexponential model using a singular value decomposition (SVD) inversion algorithm, as is common in prior art methods. For an example of an application of SVD to NMR echo trains, see U.S. Pat. No. 5,517,115 issued to Prammer. The solid circles in FIG. 1 are the samples of the noisy echo train at the echo interval of 1.2 milliseconds (ms). The noisy signal is generated from a multiexponential model NMR signal in accordance with Equation (1) below, and added zero-mean Gaussian noise, as in Equation (2) below. The standard deviation of the noise is 1.2.

The solid curves plot the underlying time-dependent noise-free multiexponential signal (thin line), and the fit to the noisy signal obtained using the SVD inversion method of the prior art (bold line). When the standard deviation of the random noise is high, the estimate noticeably misrepresents the actual spectrum. The short components of the input data, t 10 ms, suffer most, underestimating the effective porosity. This is also seen in the $T_2$ spectrum.

FIG. 1B shows an underlying bimodal distribution (dual peak) (○) and the estimated $T_2$ spectrum (×). The underlying distribution is bimodal with peaks near a $T_2$ of 3 ms and 150 ms. The multiexponential model includes seventeen terms, of which five have zero amplitude. The resulting fit to the spectrum from the SVD inversion has a single, broad, peak near $T_2$ equal to 100 msec. The $T_2$ spectrum below approximately 11 ms significantly underestimates the actual spectrum, and in the range of approximately 20–90 ms overestimates the actual spectrum.

Thus, there is a need in the art for improved methods of NMR signal processing for the recovery of $T_2$ spectra and thereby subterranean petrophysical characteristics in a oil or gas reservoir.

SUMMARY OF THE INVENTION

The previously described needs are addressed by the invention. Accordingly, a first form of the invention is a method of nuclear magnetic resonance (NMR) well log processing. The method includes the steps of forming a wavelet decomposition of NMR data signal, thereby obtaining a set of first coefficient values having a preselected first maximum scale and preselected first minimum scale; and windowing a preselected subset of the set of first coefficient values, thereby forming a windowed set of first coefficient values. A first reconstruction of the NMR signal is formed by generating an inverse wavelet transform of the windowed set of first coefficient values.

There is also provided, in a second form of the invention a computer software product for NMR well log processing including programming for forming a wavelet decomposition of NMR data, thereby obtaining a set of first coefficient values having a preselected first maximum scale and preselected first minimum scale, and programming for windowing a preselected subset of the set of first coefficient values, thereby forming a windowed set of first coefficient values. The computer software product also includes programming for generating an inverse wavelet transform of the windowed set of first coefficient values to form a first reconstruction of the NMR signal.

The method of the invention particularly addresses the need for resolving bimodal distributions involving short and long $T_2$ components, and for narrow monomodal distributions (often related to gas or light oil in a formation) that are broadened by noise and regularization. Improved bimodal distributions are useful for hydrocarbon typing involving either oil and gas, water and gas, or oil and water saturations. Sharpening monomodal distributions is useful in determining the $T_2$ value of the fluid phase thereby improving viscosity estimation.

The foregoing has outlined rather broadly the features and technical advantages of the invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which.

DESCRIPTION OF THE PREFERRED EMBODIMENTS

The invention provides a method for processing NMR well log signals. A wavelet transform of the NMR signal is generated and noise reduction is effected by windowing a preselected set of values in the wavelet decomposition. A denoised signal is reconstructed from the windowed wavelet decomposition and the reconstructed signal is fit to a multiexponential representation in order to obtain a relaxation, $T_2$, spectrum. The output signal resulting from the fit is then subject to iterated wavelet decomposition, reconstruction, and fitting sequences in which the level of the decomposition increases at each iteration. After a preselected number of iterations, a final $T_2$ spectrum and fitted NMR log signal is output. From this signal, and the $T_2$ spectrum, petrophysical parameters may be estimated.

In the following description, numerous specific details are set forth to provide a thorough understanding of the invention. However, it will be readily apparent to those skilled in the art that the invention may be practiced without such specific details.

Figure 2:
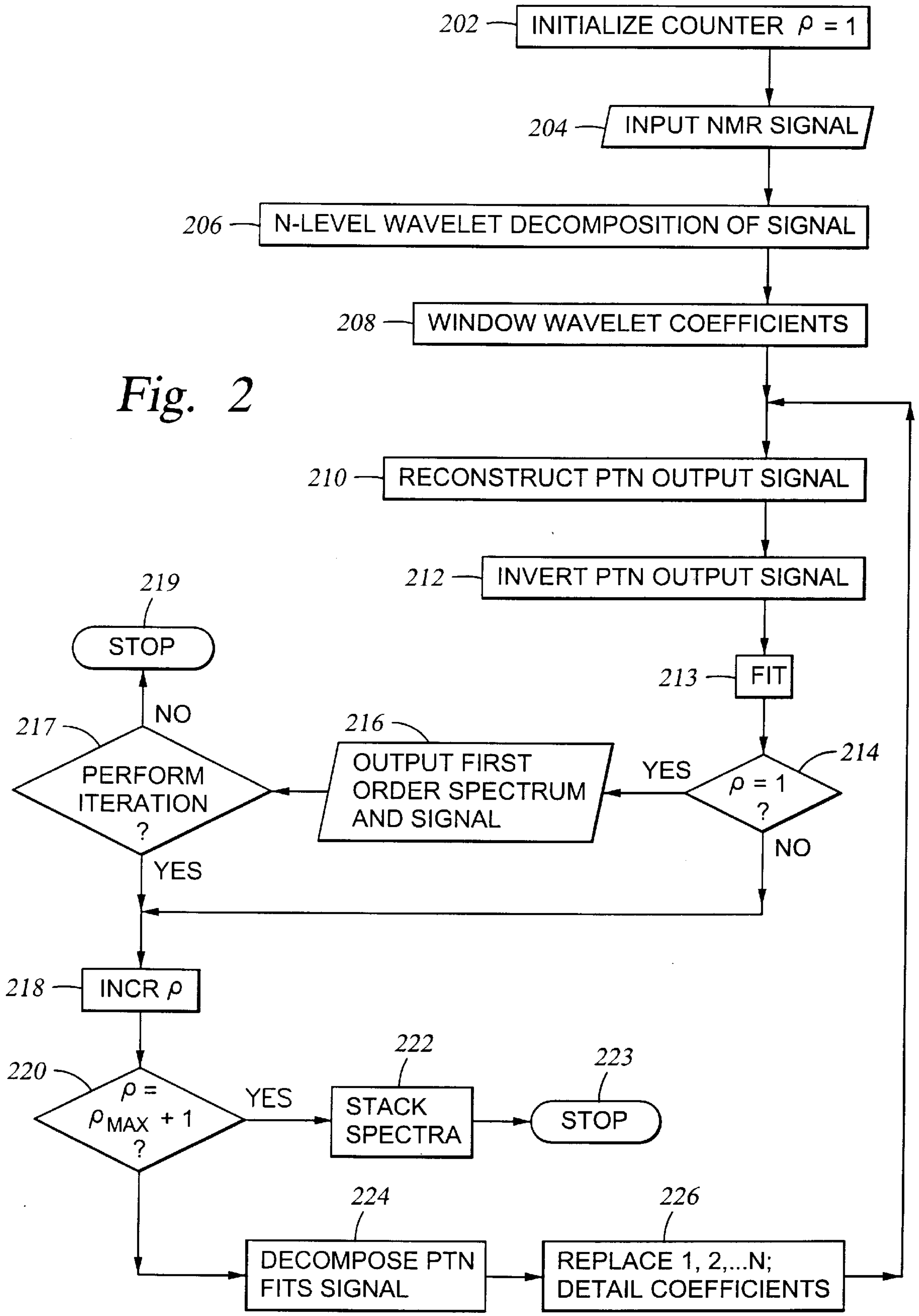
FIG. 2 illustrates, in flowchart form, an NMR log process in accordance with a method of the invention.

Refer now to FIG. 2 which illustrates a flowchart of a method of NMR log processing 200 in accordance with the principles of the present invention. Process 200 starts in step 202 with an initialization of a counter. In step 204, the NMR log signal is input.

Typical NMR log data consists of a series of echoes acquired at different times. Ideally, the echo train can be represented by a multiexponential relaxation model:

$$M(nT_E)=A_1\exp\left(-\frac{nT_E}{T_{21}}\right)+A_2\exp\left(-\frac{nT_E}{T_{22}}\right)+\ldots+A_k\exp\left(-\frac{nT_E}{T_{2k}}\right)+\ldots+A_K\exp\left(-\frac{nT_E}{T_{2k}}\right) \quad (1)$$

M is the echo amplitude, which may constitute a preselected number, k, of decaying exponential terms, each having an associated amplitude $A_k$ corresponding to a respective partial porosity. $T_E$ represents the echo interval, and $M(nT_E)$ represents the echo amplitude of the nth echo. $T_{2k}$ is the kth transverse relaxation time.

The observed signal, $Y(nT_E)$, is an echo amplitude as in Equation (1), corrupted by noise:

$$Y(nT_E)=M(nT_E)+v \quad (2)$$

A random noise signal is represented by P. The observed signal, Y of Equation (2) corresponds to the signal input in step 204. It is understood that Equation (2) is representative in that only the measured, or observed, signal Y is available. There is no independent measurement of either the noise, p, or the uncorrupted echo amplitude, M. An inversion technique, which may employ a singular value decomposition (SVD) algorithm, may be used to obtain the partial porosities, $A_k$, and the relaxation spectrum, $T_{2k}$, in Equation (1). The inversion step will be discussed further below, in conjunction with step 212.

In step 206, a N-level wavelet decomposition of the signal input in step 204 is formed. Step 206 outputs a set of detail coefficients having N members, $cD_N$, $CD_{N-1}$, $cD_{N-2}$, . . . $c_{D1}$. N is a preselected integer value. The wavelet decomposition in step 206 may be formed from a discrete wavelet transform ("DWT"). Additionally, step 206 outputs an approximation coefficient, $cA_N$. Each of the detail coefficients $cD_i(j)$, i=1,2, . . . ,N, and the approximation coefficient $cA_N(j)$, depend on a scaled time that takes on discrete values, indexed by the index j. The index j takes values in the set $[0,1, \ldots, j_{max}(i)]$ where, at each level, j takes on a maximum value, $j_{max}$ that depends on the level i. For an NMR echo train extending to a maximum time, $T_{max}$, $j_{max}(i)$ is the nearest integer value less than $T_{max}/2^i$.

Alternatively, in step 206, a wavelet decomposition of the signal input in step 204 may be formed from a continuous wavelet transform ("CWT"). In such an embodiment, step 206 outputs a coefficient, C(a,b) that is a function of two continuous variables, the scale a, and a position in time b. Although a and b are continuous, it would be understood that any realization of a data processing system for continuous wavelet transformations necessarily implicates a discrete approximation because of the finite precision arithmetic therein.

Moreover, both the DWT and CWT may be encompassed within a general framework of wavelet transforms. In the DWT, the index i indexes a discrete scale set which is in a one—one correspondence with the set of coefficient values, $cD_i$. In other words, the set of coefficient values $cD_i$ is a range set with the domain set being the set of scales indexed by i. Similarly, in the CWT, a may be considered a continuous scale index indexing a set of coefficient values, C(a,b). In the DWT, i indexes the scale between preselected minimum and maximum scales, corresponding to i=1, and i=N, respectively. Likewise, in the continuous case, the scale a may span a preselected interval ($a_{min}$, $a_{max}$) between preselected minimum and maximum scales. In an embodiment of the present invention, $a_{min}$ may be zero. It would be understood that any practical realization of a wavelet transform necessitates that $a_{max}$ be finite, although formal definitions in the art may admit scales extending to infinitely large values.

In step 208, in a DWT embodiment, the detail coefficients obtained in step 206 are windowed. The preselected subset of the $cD_i$ define a first index, $i_l$ and an integer L corresponding to a maximum index in the subset. (See, for example, Equation (3), below). In an embodiment of the present invention, the windowing function may be the function which maps each member of the preselected subset into the value 0. A preselected subset of the detail coefficients $CD_N$, $cD_{N-1}$, $CD_{N-2}$, . . . $cD_i$ are multiplied by a predetermined windowing function, w. That w is defined by:

$$w=0,\ i\epsilon\{i_1, i_1+1, \ldots, i_1+L\} \tag{3}$$

where i indexes the $cD_i$ and $$1 i_1,\ i_1+L<N$$

Alternatively, in an embodiment employing a CWT in step 206, the corresponding windowing function would take the value zero in a preselected interval of the variable a, ($a_1$, $a_2$), and the coefficient C(a,b) is windowed by multiplying C(a,b) by w. Outside of the interval ($a_1$, $a_2$) the corresponding windowing function takes the value one, thus:

$$w(a)=0,\ a\epsilon(a_1, a_2) \tag{4}$$

$$=1,\ \text{otherwise}$$

Windowing functions such as in Equation (3) and Equation (4) may be suitable for NMR signals having a $T_2$ distribution lying in a range that is larger than the window length. In a DWT embodiment, having a windowing function in accordance with Equation (3), the window length is L. A CWT embodiment with a window function according to Equation (4) has a window length of $a_2-a_1$.

In another embodiment of the present invention, a windowing function defined in Equation (5) may be used:

$$\bar{y}=\text{sign}(y)(|y|-\Lambda_m),\ |y|>\Lambda_m \tag{5}$$

$$=0,\ |y|\leqq\Lambda_m,\ m=1, 2, \ldots, n\leqq N$$

In Equation (5), m indexes the preselected subset of detail coefficients that are to be windowed. The subset of detail coefficients includes a number, n, of members, and n is less than or equal to N, the number of detail coefficients. The $\Lambda_m$ are a set of threshold values which, in an embodiment of the present invention, may have a different preselected value for each member of the subset of detail coefficients to be windowed.

The corresponding windowing function in an embodiment wherein the wavelet decomposition of step 206 is a CWT is defined by:

$$\bar{y}=\text{sign}(y)(|y|-\Lambda(a)),\ |y|>\Lambda(a), \tag{6}$$

In such an embodiment, Λ(a) is a preselected threshold function that may depend on the scale, a.

In another embodiment of the present invention, yet another windowing function may be used which yields detail coefficients in accordance with Equation (7):

$$\overline{cD}_i(j_i)=cD_i(j_i)\exp(-j_i/\tau),\ j=1,2, \ldots, j_{max}(i) \tag{7}$$

In an embodiment using a CWT in step 206, the corresponding windowed coefficients becomes:

$$\overline{C}(a,b)=C(a,b)\exp(-b/\tau)b_1(a)<b<b_2(a) \tag{8}$$

$$=C(a,\ b),\ \text{otherwise}$$

where $b_1$ and $b_2$ are preselected functions of a that define a temporal region, depending on the scale a, over which the coefficient C(a,b) is to be windowed.

In both Equation (7) and Equation (8), τ is a preselected window decay constant. In one embodiment of the present invention, τ may have the value 4.

A reconstruction of the NMR signal is generated in step 210. The reconstruction is formed, in an embodiment using a DWT for generating the decomposition, by taking the inverse discrete wavelet transform ("IDWT") of the set of windowed detail coefficients formed in step 208, and the approximation coefficient from the signal decomposition in step 206. In an embodiment wherein a CWT decomposition was formed in step 706, the reconstruction is generated from the inverse continuous wavelet transform ("ICWT") of the windowed coefficient C(a,b) from step 208.

The reconstructed signal from step 210 is inverted in step 212 to provide an estimate of the $T_{2k}$ spectrum and the set of partial porosities, $A_k$. Substitution of the values of the relaxation spectrum and partial porosities obtained in the inversion step 212 into the multiexponential model of the form in Equation (1) provides a fitted NMR signal, in step 213.

If, in step 214, the spectrum from step 212, and the fitted signal from step 213, are the first order estimates, the spectrum and fitted signal are output in step 216.

In an embodiment of the present invention, additional refinements of the spectrum and fitted NMR signal may be had. If further refinements are not desired, step 217, method 200 stops in step 219. Otherwise, the counter is incremented in step 218, and in step 220 if the counter has not exceeded a preselected maximum number of iterations, method 200 continues in step 224 by forming a wavelet decomposition of the fitted NMR signal from step 213. otherwise, in step 222 the "$p_{max}$th" estimation of the relaxation spectrum, $T_{2k}$, and fitted NMR signal are output in step 222, and method 200 stops in step 223.

In the case that the current iteration has not exceeded a preselected maximum, and the "pth" fitted signal is decomposed in step 224, a new set of detail coefficients, and a new approximate coefficient is obtained. The number of detail coefficients in the new set depends on the level of the decomposition in step 224. In an embodiment of the present invention, the level of the decomposition in step 224 may depend on the iteration number. That is, the levels in step 224 constitute a preselected set of levels, $N_p$, indexed by p with p=2, . . . , $p_{max}$. The wavelet decomposition in step 224 yields a set of detail coefficients having $N_p$ members, $cD_{N_p}^{P}$, $cD_{N_p-1}^{P}, \ldots, cD_1^{P}$. The wavelet decomposition in step 224 also yields an approximation coefficient, $cA_{N_j}^{P}$.

In step 226, the first $N_p$ detail coefficients from the previous, "(p-1)st", iteration are replaced by the detail coefficients obtained in step 224.

Alternatively, in an embodiment in which the decomposition, in step 206, is performed using a CWT further refinements are generated by forming iterated CWTs of successive fitted NMR signals. In step 224, a CWT of the fitted signal is performed to form a coefficient $C^p(a,b)$ with the scale a in an interval $(0, a_{maxp})$ where $a_{mapx} < a_{max}$ is a preselected maximum scale at the pth iteration. At the pth iteration, $a_{maxp} > a_{max(p-1)}$.

In step 226, the coefficient from the (p-1)st iteration, is replaced, for $a \in (0, a_{maxp})$ by $C^p(a,b)$. That is, at the pth iteration, the refined coefficient $C'^p(a,b)$ is defined by:

$$\begin{aligned} C'^p(a,b) &= C^p(a,b),\ 0<a<a_{maxp} \\ & 0<b<b_{max} \\ &= C(a,b),\ a_{maxp}<a<a_{max} \\ & 0<b<b_{max} \end{aligned} \tag{9}$$

where C(a,b) is the coefficient from step 206.

Method 200 then continues with the "pth" iteration, in step 210. Steps 210, 212, 213, 214 complete the pth iteration. Steps 218, 220, 224, 226, 210, 212, 213, 214 and 218 repeat until the preselected number of iterations, $p_{max}$, have been carried out. In an embodiment of the present invention, the relaxation spectrum output at each iteration, in step 217, may be averaged, in step 222. Averaging, which may also be referred to as stacking, may be taken over as subset of a set of iteration spectra output in step 217. The subset of spectra included in the average, or stack, may have a preselected number of members, $N_{dep}$, where $p_{max} \geqq N_{dep} \geqq 2$. $N_{dep}$ is referred to as the stack depth. Method 200 then terminates in step 223.

Figure 3:
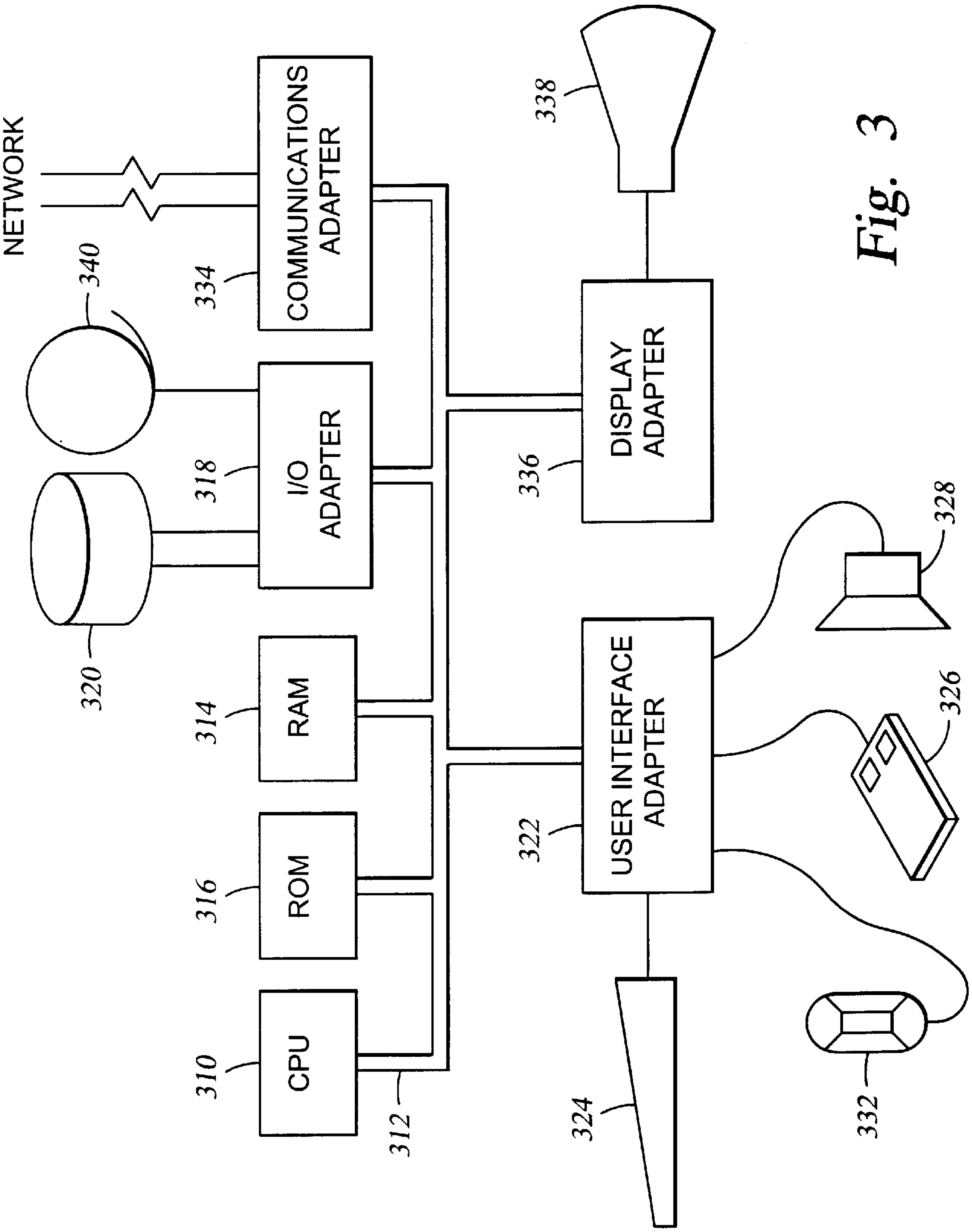
FIG. 3 illustrates, in block diagram form, a data processing system in accordance with one embodiment of the invention.

Referring first to FIG. 3, an example is shown of a data processing system 300 which may be used for the invention. The system has a central processing unit (CPU) 310. The CPU 310 is coupled to various other components by system bus 312. Read only memory ("ROM") 316 is coupled to the system bus 312 and includes a basic input/output system ("BIOS") that controls certain basic functions of the data processing system 300. Random access memory ("RAM") 314, I/O adapter 318, and communications adapter 334 are also coupled to the system bus 312. I/O adapter 318 may be a small computer system interface ("SCSI") adapter that communicates with a disk storage device 320. Communications adapter 334 interconnects bus 312 with an outside network enabling the data processing system to communication with other such systems. NMR signals for processing by the methods of the present invention may be input via communications adapter 334 from a logging tool for real-time processing, or from a database for post processing. Input/Output devices are also connected to system bus 312 via user interface adapter 322 and display adapter 336. Keyboard 324, track ball 332, mouse 326 and speaker 328 are all interconnected to bus 312 via user interface adapter 322. Display monitor 338 is connected to system bus 312 by display adapter 336. In this manner, a user is capable of inputting to the system throughout the keyboard 324, trackball 332 or mouse 326 and receiving output from the system via speaker 328 and display 338. Additionally, an operating system is used to coordinate the functions of the various components shown in FIG. 3.

Preferred implementations of the invention include implementations as a computer system programmed to execute the method or methods described herein, and as a computer program product. According to the computer system implementation, sets of instructions for executing the method or methods are resident in the random access memory 314 of one or more computer systems configured generally as described above. Until required by the computer system, the set of instructions may be stored as a computer program product in another computer memory, for example, in disk drive 320 (which may include a removable memory such as an optical disk or floppy disk for eventual use in the disk drive 320). Further, the computer program product can also be stored at another computer and transmitted when desired to the user's work station by a network or by an external network such as the Internet. One skilled in the art would appreciate that the physical storage of the sets of instructions physically changes the medium upon which it is stored so that the medium carries computer readable information. The change may be electrical, magnetic, chemical or some other physical change. While it is convenient to describe the invention in terms of instructions, symbols, characters, or the like, the reader should remember that all of these and similar terms should be associated with the appropriate physical elements.

Note that the invention may describe terms such as comparing, validating, selecting, identifying, or other terms that could be associated with a human operator. However, for at least a number of the operations described herein which form part of at least one of the embodiments, no action by a human operator is desirable. The operations described are, in large part, machine operations processing electrical signals to generate other electrical signals.

The method of the present invention may be further appreciated by referring now to FIGS. 4A–4D in which are depicted examples of synthetic NMR CPMG signals corrupted by random noise, and, $T_2$ spectra obtained therefrom in accordance with an embodiment of the present invention.

Figure 4A:
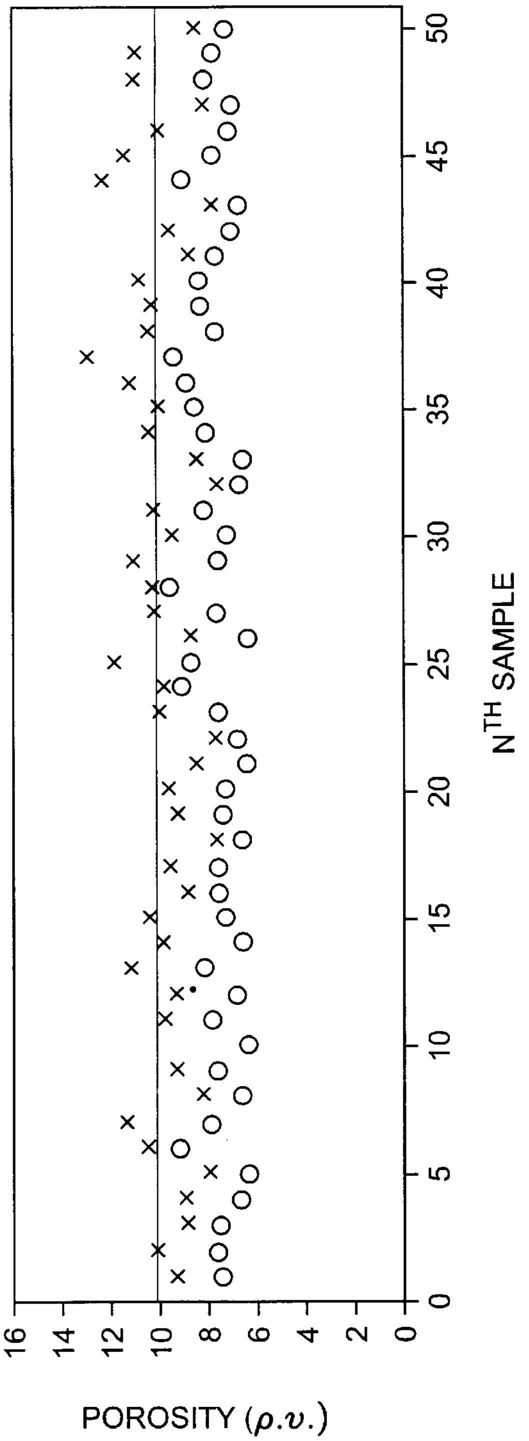
FIG. 4A graphically illustrates the effective porosity obtained from a simulated noisy NMR echo train according to an embodiment of the method of the invention.

FIG. 4A displays the effective porosity obtained from a simulated noisy NMR echo train. The solid line is the effective porosity of the underlying noise-free NMR signal, in porosity units. (Porosity units (pu) measure the porosity as a percentage.) The noise-free signal is a multiexponential model echo train in accordance with Equation (1), as will be discussed further in conjunction with FIG. 4C. The effective porosity is the sum of the coefficients $A_K$, and is approximately 10.2 for the NMR echo train displayed in FIGS. 4A–4D. The data points display the average porosity determined from fifty realizations of the noisy signal. The results are from a SVD inversion method in accordance with the prior art (○), and the method of the present invention (×). Zero-mean Gaussian noise with a standard deviation of 1.2 has been added, in accordance with Equation (2), to a synthetic multiexponential NMR signal according to Equation (1). The deviation of the average porosity values as determined by the present invention from the noise-free value are seen to be smaller than the deviation using the direct inversion SVD method. This also obtains when the effective porosity is averaged over all fifty realizations.

Figure 4B:
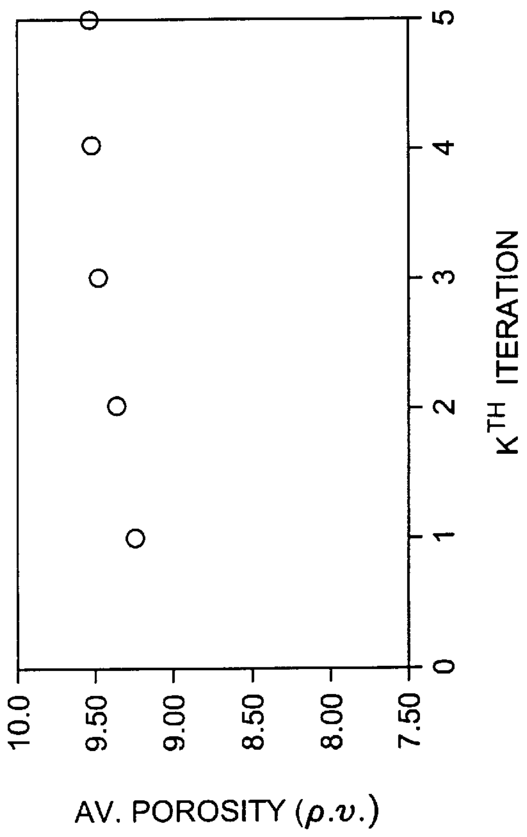
FIG. 4B graphically illustrates the mean effective porosity obtained from a simulated noisy NMR echo train according to an embodiment of the method of the invention.

The mean effective porosity is shown in FIG. 4B. The mean effective porosity is the effective porosity averaged over the fifty realizations of the noisy signal, as displayed in FIG. 4A. The mean effective porosity is shown as a function of the iteration number of the method of the present invention. Iteration number "0" corresponds to the prior art direct inversion SVD method. It is seen that the mean effective porosity asymptotes to a value of approximately 9.5 which underestimates the effective porosity of the underlying noise-free signal by seven percent (7%). This is a significant improvement over the direct inversion SVD value of approximately 7.6 which underestimates the actual value by twenty-five percent (25%).

Figure 4C:
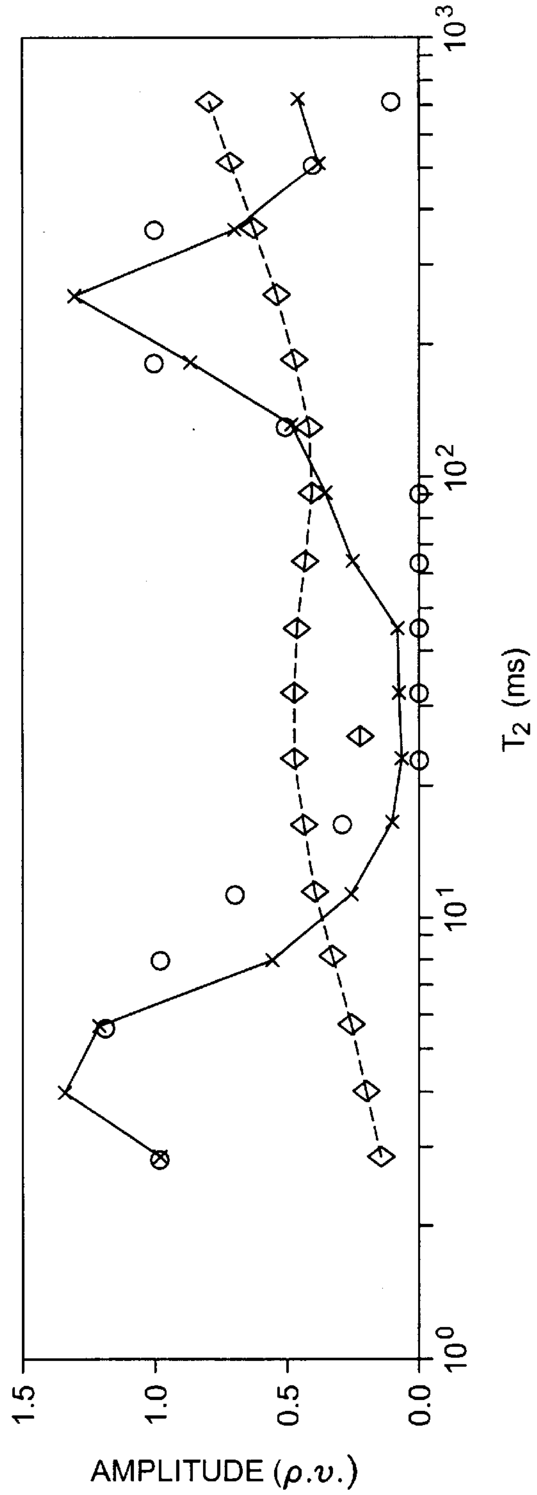
FIG. 4C graphically illustrates a $T_2$ spectrum obtained from a simulated noisy NMR echo train according to an embodiment of the method of the invention.

The $T_2$ spectrum, averaged over the fifty realizations of the noisy signal is illustrated in FIG. 4C. The underlying noise-free multiexponential in accordance with Equation (1) includes seventeen components (○), of which five have partial porosities with the value zero. The spectrum is bimodal with maxima at $T_2$ of 5 msec and 250 msec. The short-time peak corresponds to relaxation spectra due to water, and the long-time peak corresponds to relaxation spectra from oil. The averaged spectrum recovered from a direct inversion SVD (◇) does not reproduce the two-peaked, bimodal, spectrum of the underlying synthesized NMR signal. The spectrum obtained using the method of the present invention with five iterations ($p_{max}$ corresponding to five iterations in step 220, FIG. 1) generates a bimodal distribution approximating that of the uncorrupted signal.

Figure 1A:
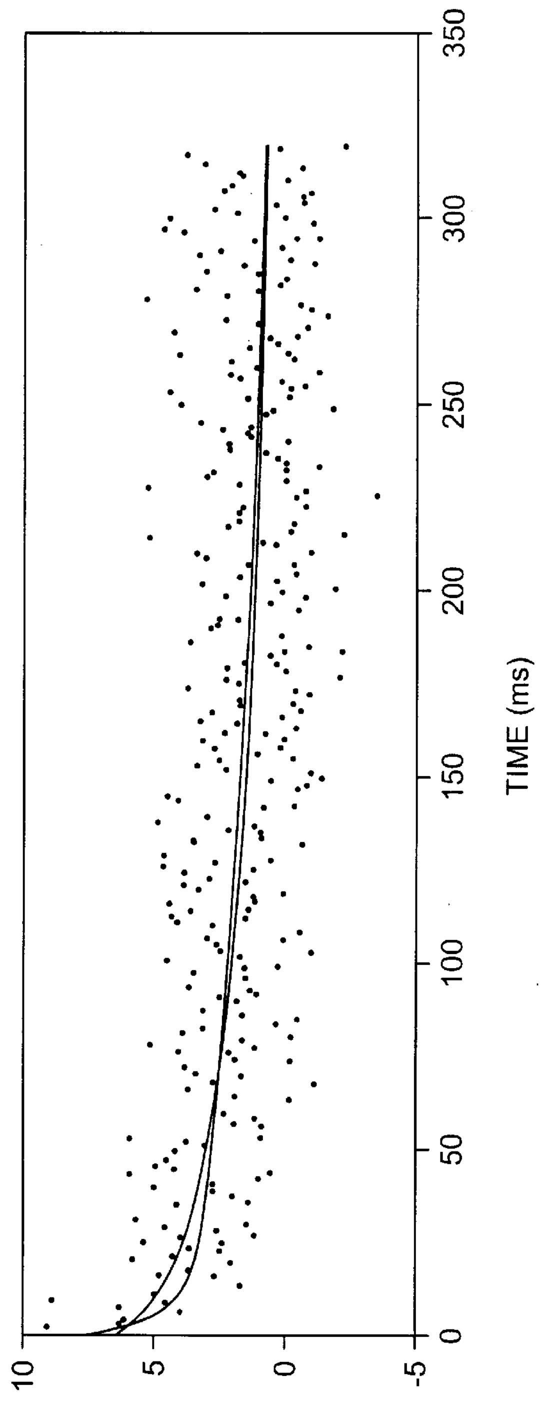
FIG. 1A illustrates a graph showing data from a simulated noisy echo train fitted using an SVD inversion method in accordance with the prior art.
Figure 1B:
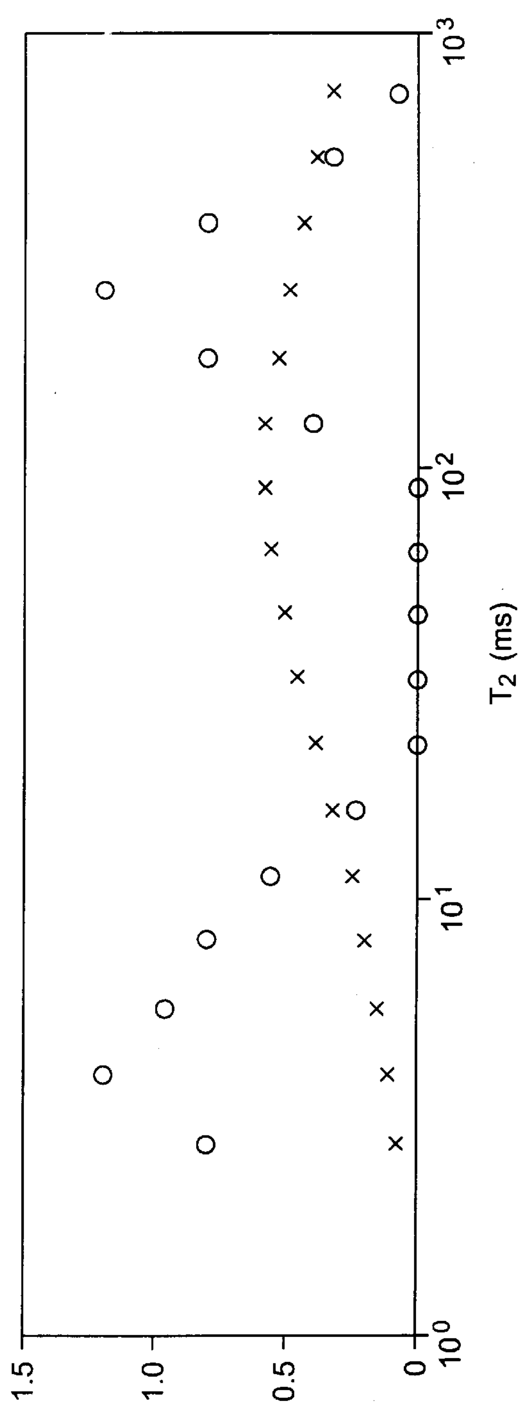
FIG. 1B illustrates a simulated multiexponential $T_2$ spectrum and the corresponding fit obtained from the noisy echo train using an SVD inversion method according to the prior art.
Figure 4D:
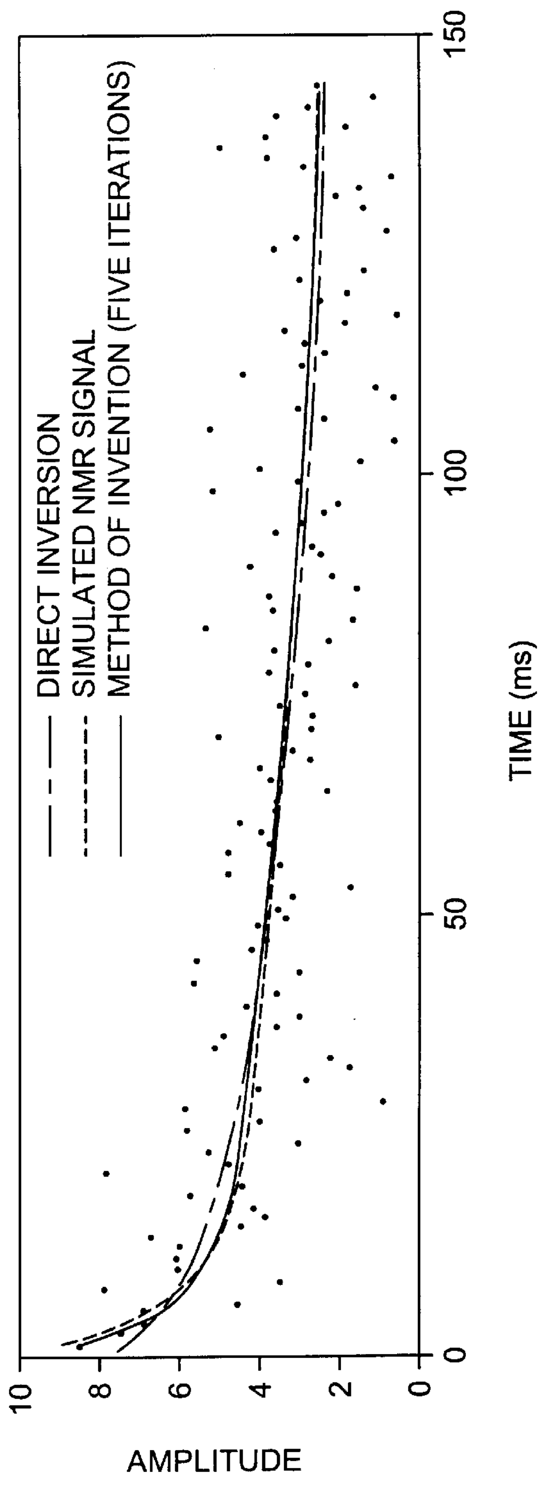
FIG. 4D graphically illustrates the simulated noisy NMR echo train and a fitted NMR signal obtained according to an embodiment of the method of the invention.

The NMR signals are shown in FIG. 4D. The signal amplitude is displayed as a function of time out to 100 echo times, or 120 msec. A single realization of the noisy signal is represented by the data points (●). The underlying synthetic NMR signal is shown by the dashed curve. The fitted signal, as described in conjunction with step 213 in FIG. 1 is shown by the solid curve. The fitted signal has been averaged over the fifty realizations to better reveal any systematic bias that might be introduced by the signal recovery methods, and corresponds to five iterations, as before. The signal resulting from the prior art direct inversion SVD is shown by the dot-dash curve. The short-time components of the NMR signal are especially misrepresented by the prior-art fit, resulting in an underestimation of the effective porosity. The fit generated by the method of the present invention yields a better reproduction of the underlying noise-free signal, particularly for times less than approximately 25 msec.

The advantages of the present method are revealed in the illustrations of FIGS. 4A–4D. Systematic biases are reduced relative to the direct inversion SVD method of the prior art. The resulting effective porosity estimates, which are of geophysical importance, are improved thereby. The method is particularly advantageous in resolving bimodal $T_2$ spectra, reducing ambiguity in hydrocarbon typing.

Although the present invention and its advantages have been described in detail, it should be understood that various changes, substitutions and alterations can be made herein without departing from the spirit and scope of the invention as defined by the appended claims.

What is claimed is:

1. A method of nuclear magnetic resonance (NMR) well log processing comprising the steps of:

forming a wavelet decomposition of an NMR data signal, thereby obtaining a set of first coefficient values having a preselected first maximum scale and a preselected first minimum scale;

windowing a preselected subset of said set of first coefficient values, thereby forming a windowed set of coefficient values; and generating an inverse wavelet transform of said windowed set of coefficient values, to form a first reconstruction of said NMR signal.

2. The method of claim 1 further comprising the step of inverting said first reconstruction to form a relaxation spectrum signal.

3. The method of claim 1 wherein said windowing step comprises the steps of:

applying a windowing function to each member of said preselected subset of first coefficient values; and substituting each member of said subset by a corresponding windowed coefficient formed in said applying step.

4. The method of claim 3 wherein said preselected subset comprises a discrete subset and wherein said step of applying a windowing function comprises the step of applying a discretely indexed windowing function to said preselected subset.

5. The method of claim 4 wherein said step of applying a windowing function comprises the step of generating windowed coefficients defined by:

$$\overline{cD_i}(j)=cD_i(j)\exp(-j/\tau),\ j=1,2,\ldots j_{max}(i),$$

wherein $j_{max}(i)$ comprises a preselected maximum length, and $\tau$ comprises a preselected decay constant.

6. The method of claim 3 wherein said preselected subset comprises a continuous subset and wherein said step of applying a windowing function comprises the step of applying a continuously indexed windowing function to said subset.

7. The method of claim 6 wherein said step of applying a windowing function comprises the step of generating windowed coefficients defined by:

$$\overline{C}(a,b)=C(a,b)\exp(-b/\tau),\ b_1(a)<b<b_2(a)$$
$$=C(a,b),\ \text{otherwise},$$

wherein $b_1$ and $b_2$ comprise preselected functions of a scale, a.

8. The method of claim 1 further comprising the step of fitting said first reconstruction to a preselected model signal to form a first fitted NMR signal.

9. The method of claim 8 wherein said step of fitting said first reconstruction includes the step of determining a set of parameter values according to a fitting algorithm.

10. The method of claim 8 further comprising the steps of:

forming a wavelet decomposition of said first fitted NMR signal, thereby obtaining a set of second coefficient values having a preselected next maximum and next minimum scale, wherein said next maximum scale is less than a previous maximum scale and said next minimum scale is not less than a previous minimum scale;

replacing a corresponding subset of said set of windowed first coefficient values by said set of second coefficient values; and forming an inverse wavelet transformation of a set of coefficients formed in said replacing step, to form a second reconstruction of said NMR signal.

11. The method of claim 10 further comprising the step of fitting said second reconstruction to said preselected model signal to form a second fitted NMR signal.

12. The method of claim 11 further comprising the step of, for a preselected number, M-2, of iterations, repeating said steps of forming said wavelet transform, replacing a corresponding subset, forming an inverse wavelet transform, and fitting to form an “Mth” fitted NMR signal.

13. The method of claim 12 further comprising the step of, for each iteration, inverting a corresponding reconstruction to form a corresponding relaxation spectrum, thereby forming an “Mth” relaxation spectrum at a last iteration.

14. The method of claim 12 wherein said wavelet transform is a discrete wavelet transform (DWT).

15. The method of claim 12 wherein said wavelet transform is a continuous wavelet transform (CWT).

16. The method of claim 10 wherein said set of second coefficient values comprises a continuously indexed set, said wavelet transform comprising a continuous wavelet transform.

17. The method of claim 10 further comprising the step of inverting said second reconstruction to form a second relaxation spectrum.

18. The method of claim 10 wherein said set of second coefficient values comprise a set of detail coefficients and wherein said wavelet decomposition of said fitted NMR signal further an approximation coefficient, said wavelet decomposition comprising a discrete wavelet transform.

19. The method of claim 1 wherein said step of forming a wavelet decomposition comprises the step of forming a discrete wavelet transform, said discrete wavelet transform further including an approximation coefficient, and wherein said set of first coefficient values includes a discrete, preselected, number of members.

20. The method of claim 19 wherein said set of first coefficients comprises a set of detail coefficients and said second coefficient comprises an approximation coefficient.

21. A computer program product operable for storage on machine readable media, the program product for nuclear magnetic resonance (NMR) well logging comprising:

programming for forming a wavelet decomposition of an NMR data signal, thereby obtaining a set of first coefficients;

programming for windowing a preselected subset of said set of first coefficient values, thereby forming a windowed set of coefficient values; and programming for generating an inverse wavelet transform of said windowed set of coefficient values, to form a first reconstruction of said NMR signal.

22. The computer program product of claim 21 further comprising programming for inverting said first reconstruction to form a relaxation spectrum signal.

23. The computer program product of claim 21 wherein said programming for windowing comprises:

programming for applying a windowing function to each member of said preselected subset of first coefficients; and substituting each member of said subset by a corresponding windowed coefficient formed in said applying step.

24. The computer program product of claim 23 wherein said preselected subset comprises a discrete subset and wherein said programming for applying a windowing function comprises programming for applying a discretely indexed windowing function to said preselected subset.

25. The method of claim 24 wherein said programming for applying a windowing function comprises programming for generating windowed coefficients defined by:

$$\overline{cD_i}(j)=cD_i(j)\exp(-j/\tau),\ j=1,2,\ \ldots\ j_{max}(i),$$

wherein $j_{max}(i)$ comprises a preselected maximum length, and $\tau$ comprises a preselected decay constant.

26. The computer program product of claim 23 wherein said preselected subset comprises a continuous subset and wherein said programming for applying a windowing function comprises the programming for applying a continuously indexed windowing function to said subset.

27. The computer program product of claim 26 wherein said programming for applying a windowing function comprises programming for generating windowed coefficients defined by:

$$\overline{C}(a,b)=C(a,b)\exp(-b/\tau),\ b_1(a)<b<b_2(a)$$

$$=C(a,b),\ \text{otherwise},$$

wherein $b_1$ and $b_2$ comprise preselected functions of a scale, a.

28. The computer program product of claim 21 further comprising programming for fitting said first reconstruction to a preselected model signal to form a first fitted NMR signal.

29. The computer program product of claim 28 wherein said programming for fitting said first reconstruction includes programming for determining a set of parameter values according to a fitting algorithm.

30. The computer program product of claim 29 further comprising:

programming for forming a wavelet decomposition of said first fitted NMR signal, thereby obtaining a set of second coefficient values having a next maximum and next minimum scale;

programming for replacing a corresponding subset of said set of windowed first coefficient values by said set of second coefficient values; and programming for forming an inverse wavelet transformation of a set of coefficients formed in said replacing step, to form a second reconstruction of said NMR signal.

31. The computer program product of claim 30 further comprising programming for fitting said second reconstruction to said preselected model signal to form a second fitted NMR signal.

32. The computer program product of claim 31 further comprising programming for, for a preselected number, M-2, of iterations, repeating said programming for forming said wavelet transform, replacing a corresponding subset, forming an inverse wavelet transform, and fitting to form an "Mth" fitted NMR signal.

33. The computer program product of claim 32 further comprising programming for, for each iteration, inverting a corresponding reconstruction to form a corresponding relaxation spectrum, thereby forming an "Mth" relaxation spectrum at a last iteration.

34. The computer program product of claim 32 wherein said wavelet transform is a continuous wavelet transform (CWT).

35. The computer program product of claim 32 wherein said wavelet transform is a discrete wavelet transform (DWT).

36. The computer program product of claim 30 further comprising programming for inverting said second reconstruction to form a second relaxation spectrum.

37. The computer program product of claim 30 wherein said set of second coefficient values comprise a set of detail coefficients and wherein said wavelet decomposition of said fitted NMR signal further an approximation coefficient, said wavelet decomposition comprising a discrete wavelet transform.

38. The computer program product of claim 30 wherein said set of second coefficient values comprises a continuously indexed set, said wavelet transform comprising a continuous wavelet transform.

39. The computer program product of claim 21 wherein said programming for forming a wavelet decomposition comprises programming for forming a discrete wavelet transform, said discrete wavelet transform further including an approximation coefficient, and wherein said set of first coefficient values includes a discrete, preselected, number of members.

40. The computer program product of claim 39 wherein said set of first coefficients comprises a set of detail coefficients and said second coefficient comprises an approximation coefficient.

* * * * *